US010751754B2

(12) United States Patent
Najar et al.

(10) Patent No.: US 10,751,754 B2
(45) Date of Patent: Aug. 25, 2020

(54) MICROMACHINED ULTRASOUND TRANSDUCER

(71) Applicant: TEXAS INSTRUMENTS INCORPORATED, Dallas, TX (US)

(72) Inventors: Mohammad Hadi Motieian Najar, Santa Clara, CA (US); Peter Smeys, San Jose, CA (US)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 485 days.

(21) Appl. No.: 15/664,637

(22) Filed: Jul. 31, 2017

(65) Prior Publication Data

US 2019/0030569 A1 Jan. 31, 2019

(51) Int. Cl.
*H01L 41/047* (2006.01)
*H01L 41/00* (2013.01)
*B06B 1/06* (2006.01)
*A61B 8/00* (2006.01)
*B06B 1/02* (2006.01)

(52) U.S. Cl.
CPC .......... *B06B 1/0618* (2013.01); *A61B 8/4483* (2013.01); *B06B 1/0292* (2013.01); *H01L 41/047* (2013.01)

(58) Field of Classification Search
CPC ... H01L 41/047; B06B 1/0618; B06B 1/0292; A61B 8/4483
USPC .......................................... 310/317, 320, 334
See application file for complete search history.

(56) References Cited

U.S. PATENT DOCUMENTS

| 3,163,783 | A   | * | 12/1964 | Howatt  | H04R 17/00 310/314 |
| 6,215,229 | B1  | * | 4/2001  | Kuroda  | H03H 3/04 310/320  |
| 9,160,305 | B1  | * | 10/2015 | Wu      | H03H 3/02          |
| 9,326,752 | B2  | * | 5/2016  | Umeda   | A61B 8/14          |
| 9,960,339 | B2  | * | 5/2018  | Naono   | H01L 41/09         |
| 2013/0049539 | A1 | * | 2/2013 | Lee     | H01L 41/1136 310/339 |
| 2017/0156636 | A1 | * | 6/2017 | Kawamura | A61B 5/11        |

* cited by examiner

*Primary Examiner* — Thomas M Dougherty
(74) *Attorney, Agent, or Firm* — Michael A. Davis, Jr.; Charles A. Brill; Frank D. Cimino

(57) ABSTRACT

A hybrid micromachined ultrasound transducer includes a piezoelectric micromachined transducer and a capacitive micromachined transducer. The capacitive micromachined transducer is vertically stacked with the piezoelectric micromachined transducer. The piezoelectric micromachined transducer and the capacitive micromachined transducer include a common shared electrode.

20 Claims, 6 Drawing Sheets

MICROMACHINED ULTRASOUND TRANSDUCER

BACKGROUND

Ultrasound is used in a wide variety of applications. For example, ultrasound imaging is widely used to image internal structures in a variety of applications. Use of ultrasound in medical imaging is one common application. An ultrasound system typically includes a transceiver housed in a probe. An ultrasound probe usually includes an array of transducer elements. An electrical signal applied to a transducer element causes the element to produce an acoustic signal corresponding to the electrical signal. Similarly, an acoustic signal incident on the transducer element causes the element to produce an electrical signal representative of the incident acoustic signal.

SUMMARY

A hybrid micromachined ultrasound transducer is disclosed herein. In one embodiment, a micromachined ultrasound transducer includes a piezoelectric micromachined transducer and a capacitive micromachined transducer. The capacitive micromachined transducer is vertically stacked with the piezoelectric micromachined transducer. The piezoelectric micromachined transducer and the capacitive micromachined transducer include a common shared electrode.

In another embodiment, an ultrasound transducer includes a capacitive micromachined transducer and a piezoelectric micromachined transducer. The piezoelectric micromachined transducer is disposed above and is laterally aligned with the capacitive micromachined transducer in a stack of micromachined layers.

In a further embodiment, a method includes driving a first electrode and a second electrode of a first micromachined transducer to generate an ultrasonic signal. A reflection of the ultrasonic signal is detected via a second micromachined transducer that is vertically stacked with the first micromachined transducer in a hybrid micromachined ultrasound transducer. An electrical signal representative of the detected reflection of the ultrasonic signal is provided via the second electrode and a third electrode. The second electrode serves as an electrode of the first micromachined transducer and an electrode of the second micromachined transducer.

BRIEF DESCRIPTION OF THE DRAWINGS

For a detailed description of various examples, reference will now be made to the accompanying drawings in which.

DETAILED DESCRIPTION

Certain terms are used throughout the following description and claims to refer to particular system components. As one skilled in the art will appreciate, different parties may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . " Also, the term "couple" or "couples" is intended to mean either an indirect or direct wired or wireless connection. Thus, if a first device couples to a second device, that connection may be through a direct connection or through an indirect connection via other devices and connections.

Piezoelectric and capacitive transducers are well known in ultrasound systems and can be constructed using micro-electro-mechanical system (MEMS) fabrication processes. While piezoelectric micromachined ultrasound transducers and capacitive micromachined ultrasound transducers each exhibit distinct advantages relative to the other, each is also subject to various shortcomings. For example, capacitive micromachined ultrasound transducers provide high sensitivity that results in good acoustic signal receptivity, but the structural characteristics that produce the high sensitivity tend to limit the capacitive micromachined ultrasound transducer's transmission capabilities. Similarly, piezoelectric micromachined ultrasound transducers provide good acoustic signal generation capabilities, but have reduced sensitivity to acoustic signals relative to capacitive micromachined ultrasound transducers. Conventional solutions focus on structural or material variations of the piezoelectric or capacitive transducers in an attempt to improve performance. Unfortunately, such solutions add undesirable complexity.

Embodiments of a hybrid micromachined transducer that provides the advantages of both piezoelectric and capacitive micromachined ultrasound transducers are disclosed herein. The hybrid micromachined transducer includes a piezoelectric micromachined transducer vertically stacked with a capacitive micromachined transducer. Thus, the hybrid micromachined transducer provides the transmission capabilities of a piezoelectric micromachined transducer and the reception sensitivity of a capacitive micromachined transducer within the same area occupied by a conventional piezoelectric micromachined transducer or capacitive micromachined transducer, and with substantially lower complexity than laterally adjacent piezoelectric micromachined transducers and capacitive micromachined transducers. Embodiments of the hybrid micromachined ultrasound transducer may be highly advantageous in high resolution ultrasound systems that employ transducer arrays including hundreds or thousands of ultrasound transducers.

Figure 1:
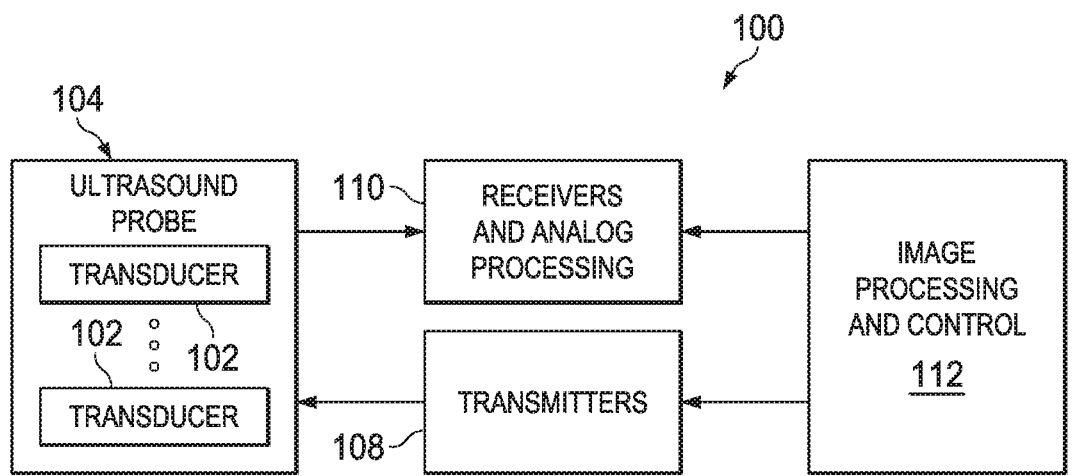
FIG. 1 shows a block diagram of an ultrasound imaging system in accordance with various embodiments.

FIG. 1 shows a block diagram of an ultrasound imaging system 100 in accordance with various embodiments. The ultrasound imaging system 100 is one of many different applications for which the hybrid micromachined ultrasound transducer disclosed herein is suitable. Ultrasound systems use amplitude and phase information from reflected acoustic waves to provide structural and functional information about an object of interest. The ultrasound imaging system 100 includes an ultrasound probe 104, transmitters 108, receivers and analog processing circuitry 110, and image processing and control circuitry 112. The ultrasound probe 104 includes a plurality of hybrid micromachined ultrasound transducers 102. For example, the ultrasound probe 104 may include hundreds or thousands of hybrid micromachined ultrasound transducers 102. Each of the hybrid micromachined ultrasound transducers 102 is capable of converting an electrical signal into an acoustic signal and converting an acoustic signal into an electrical signal. Thus, each of the hybrid micromachined ultrasound transducers 102 serves as an ultrasound transceiver.

The transmitters 108 are drivers that provide electrical signals to induce generation of acoustic signals by the hybrid micromachined ultrasound transducers 102. Each of the transmitters 108 drives one or more of the hybrid micromachined ultrasound transducers 102.

The receivers and analog processing circuitry 110 includes receiver circuitry that receives electrical signals generated by the hybrid micromachined ultrasound transducers 102 responsive to incident acoustic energy and analog processing circuitry that manipulates receiver signal output. In some embodiments, the receiver circuitry includes low noise amplifiers, amplifier gain control circuitry (e.g., variable gain amplifiers and associated control), etc. In some embodiments, the analog processing circuitry includes filters (e.g., anti-alias filters) and analog-to-digital conversion circuitry to digitize the received ultrasound signals.

The image processing and control circuitry 112 controls the generation of transducer drive signals by the transmitters 108, and processes the received ultrasound signals provided by the receivers and analog processing circuitry 110. The image processing and control circuitry 112 may include transmit and/or receive beamforming circuitry to focus the transmitted and/or received ultrasound signals, brightness mode ("B-mode") imaging circuitry and/or color Doppler mode imaging circuitry, and other processing circuitry to manipulate image data and present images on a display device for viewing and interpretation by a user.

In at least some embodiments of the ultrasound imaging system 100, the image processing and control circuitry 112 includes a processor, such as a digital signal processor that executes instructions to provide the functionality of the B-mode imaging circuitry, color Doppler mode imaging circuitry, and/or other processing applied to received or transmitted ultrasound signals. Instructions can be stored in a computer readable medium, such as a semiconductor memory device, a magnetic or optical storage device, or other storage device accessible to the processor. In some embodiments, at least some of the operations of the image processing and control circuitry 112 are implemented in dedicated hardware circuitry, such as an application specific integrated circuit ("ASIC") or field programmable gate array ("FPGA").

The hybrid micromachined ultrasound transducer 102 can be applied in a wide variety of ultrasound applications. The ultrasound imaging system 100 is described herein as one example of an application in which the hybrid micromachined ultrasound transducer 102 can be used. Other applications for which the hybrid micromachined ultrasound transducer 102 is suitable include structural inspection systems, echolocation systems, distance measurement systems, and other applications in which a compact and efficient ultrasound transducer is desirable.

Figure 2:
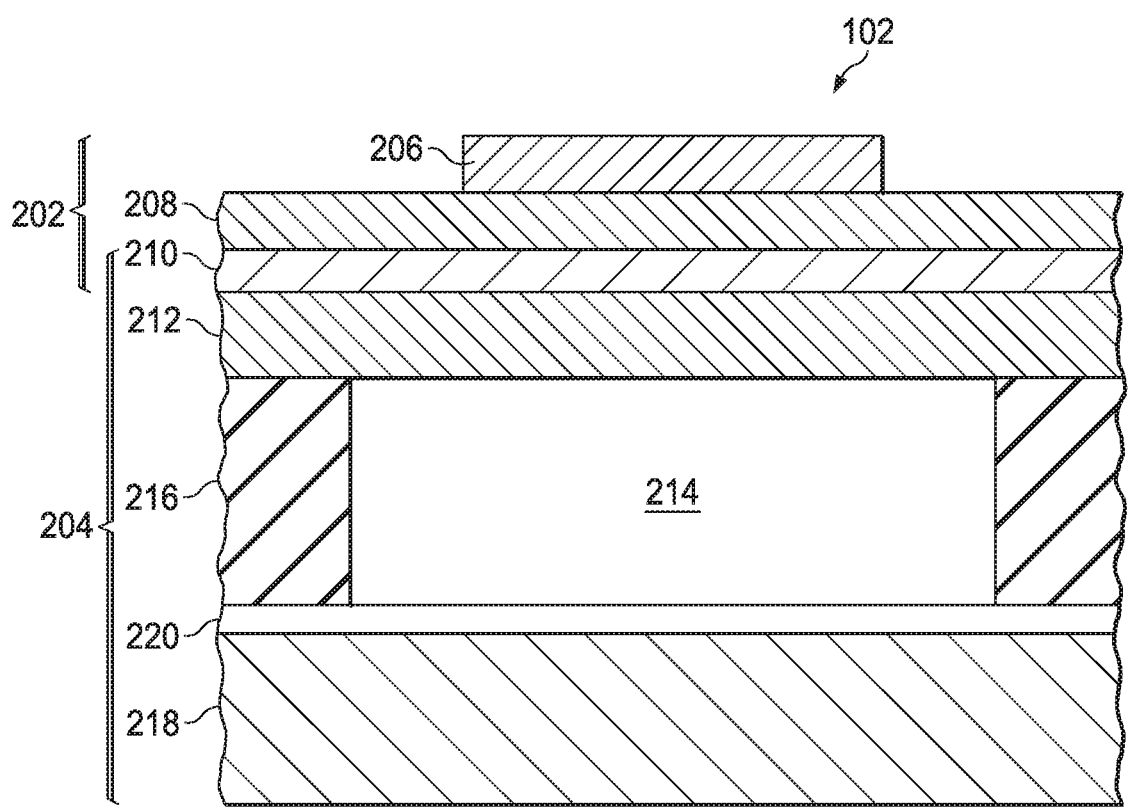
FIG. 2 shows a cross-sectional view of a hybrid micromachined ultrasound transducer in accordance with various embodiments.

FIG. 2 shows a cross-sectional view of a hybrid micromachined ultrasound transducer 102 accordance with various embodiments. The hybrid micromachined ultrasound transducer 102 includes a piezoelectric micromachined transducer 202 and capacitive micromachined transducer 204. The piezoelectric micromachined transducer 202 and capacitive micromachined transducer 204 are fabricated in a stack of micromachined layers with the piezoelectric micromachined transducer 202 formed above and laterally aligned with the capacitive micromachined transducer 204. Because the piezoelectric micromachined transducer 202 and capacitive micromachined transducer 204 are vertically stacked the hybrid micromachined ultrasound transducer 102 provides the piezoelectric micromachined transducer 202 and capacitive micromachined transducer 204 in no more lateral area than a single conventional capacitive micromachined ultrasound transducer or piezoelectric micromachined ultrasound transducer. The term "vertically stacked" refers to the direction in which layers are built-up or "stacked" in the hybrid micromachined ultrasound transducer 102. The hybrid micromachined ultrasound transducer 102 includes three electrodes that provide the electrical connections to the piezoelectric micromachined transducer 202 and capacitive micromachined transducer 204. The three electrodes include a top or upper electrode 206, a middle electrode 210, and a bottom or lower electrode 218. The middle electrode 210 is shared by the piezoelectric micromachined transducer 202 and capacitive micromachined transducer 204 and is also referred to herein as a common shared electrode 210 or an intermediate electrode 210.

The piezoelectric micromachined transducer 202 includes the upper electrode 206, the middle electrode 210, and a piezoelectric layer 208. The piezoelectric layer 208 is disposed between the upper electrode 206 and the middle electrode 210. Voltage across the upper electrode 206 and the middle electrode 210 causes the piezoelectric layer 208 to flex. Accordingly, AC voltage induced across the upper electrode 206 and the middle electrode 210 produces ultrasound signal generation by the piezoelectric micromachined transducer 202. Similarly, ultrasound signal incident on the piezoelectric layer 208 causes the piezoelectric layer 208 to flex and induce voltage across the upper electrode 206 and the middle electrode 210 to allow use of the piezoelectric micromachined transducer 202 as an ultrasound receiver. In some embodiments, the upper electrode 206 and the middle electrode 210 are formed of molybdenum, and the piezoelectric layer 208 is formed of aluminum nitride. In some embodiments, different materials may be used to form the upper electrode 206, the middle electrode 210, and the piezoelectric layer 208.

The capacitive micromachined transducer 204 includes the middle electrode 210, a structural plate 212, an insulation layer 216, a cavity or vacuum gap 214 formed between the structural plate and the insulation layer 216, and a lower electrode 218 formed from the substrate of the hybrid micromachined transducer 102. In some embodiments of the hybrid micromachined ultrasound transducer 102, the capacitive micromachined transducer 204 includes an insulation layer 220. The middle electrode 210 and the lower electrode 218 serve as the plates of the capacitive micromachined transducer 204. The cavity 214 serve as the dielectric of the capacitive micromachined transducer 204. Voltage across the middle electrode 210 and the lower electrode 218 causes the structural plate 212 to flex (e.g., due to electrostatic force). Accordingly, AC voltage induced across the middle electrode 210 and the lower electrode 218 produces ultrasound signal generation by the capacitive micromachined transducer 204. Ultrasound signal incident on the structural plate 212 causes the structural plate 212 to flex and induce voltage across the middle electrode 210 and the lower electrode 218 to allow use of the capacitive micromachined transducer 204 as an ultrasound receiver. A DC voltage applied across the middle electrode 210 and the lower electrode 218 generates an electrostatic force that pulls the middle electrode 210 towards the lower electrode 218, thereby reducing the distance between the middle electrode 210 and the lower electrode 218 and increasing the sensitivity of the capacitive micromachined transducer 204 for use as both an ultrasound receiver and ultrasound transmitter. The insulation layer 220 prevents shorting of the electrode 218 and the structural plate 212. In some embodiments the substrate 218 and the structural plate 212 are formed of silicon and the insulation layers 216 and 220 are formed of silicon dioxide. In some embodiments, different materials may be used to form the substrate 218, the structural plate 212, and the insulation layers 216 and 220.

Embodiments of the ultrasound imaging system 100 apply the hybrid micromachined ultrasound transducer 102 in a variety of ways to generate and sense ultrasound signals. For transmission of ultrasound signal, in some embodiments, the transmitters 108 drive only the upper electrode 206 and the middle electrode 210 to apply the piezoelectric micromachined transducer 202 as an ultrasound transmitter. Alternatively, the transmitters 108 drive the upper electrode 206, the middle electrode 210, and the lower electrode 210 to simultaneously apply the piezoelectric micromachined transducer 202 and the capacitive micromachined transducer 204 as an ultrasound transmitter. For detection of ultrasound signal, in some embodiments, the receivers and analog processing circuitry 110 receive signal only from the middle electrode 210 and the lower electrode 210 to apply the capacitive micromachined transducer 204 as an ultrasound receiver. Alternatively, the receivers and analog processing circuitry 110 receive signal from the upper electrode 206, the middle electrode 210, and the lower electrode 210 to simultaneously apply the piezoelectric micromachined transducer 202 and the capacitive micromachined transducer 204 as an ultrasound receiver.

Figure 3:
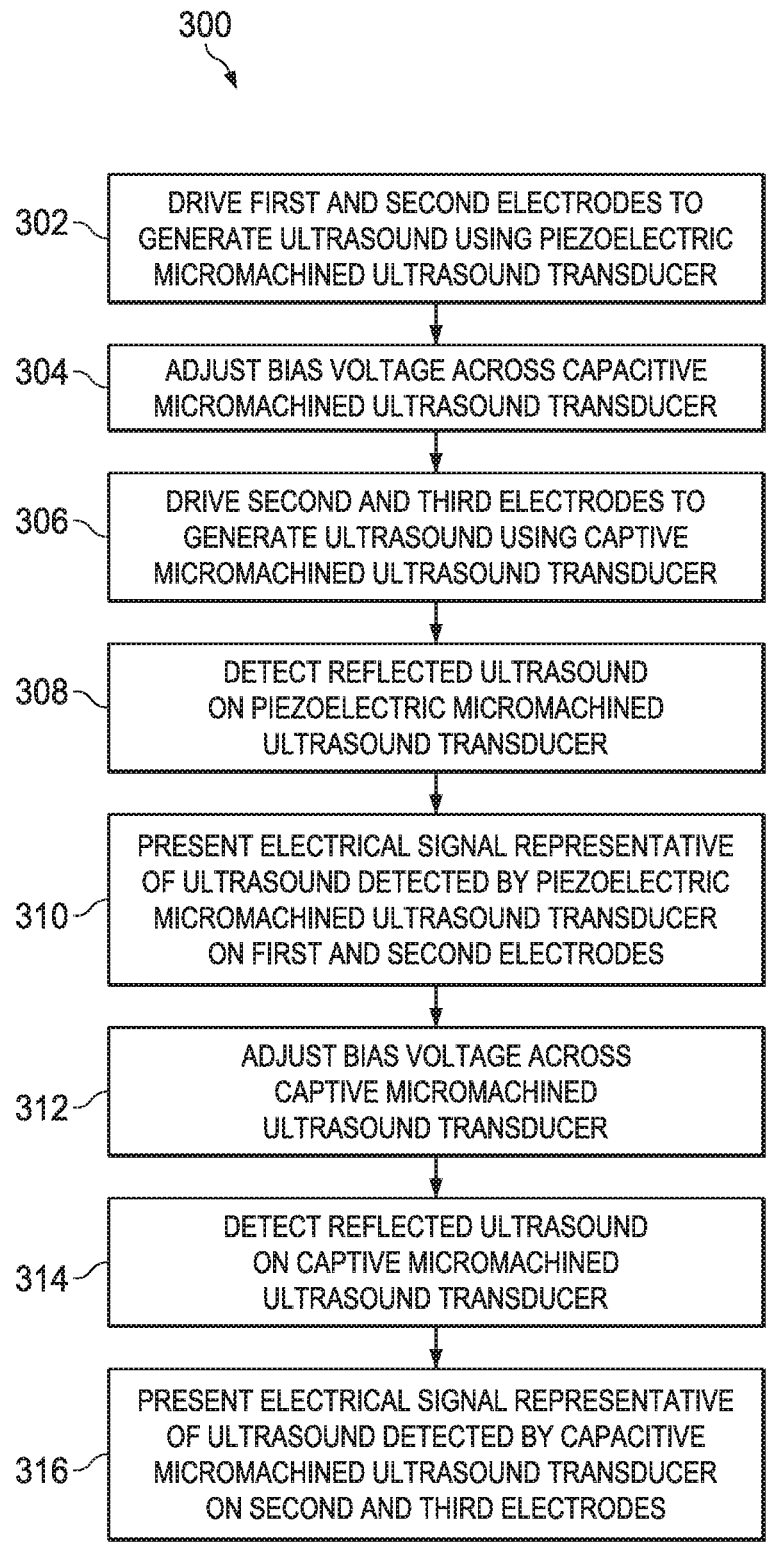
FIG. 3 shows a flow diagram for a method of operating a hybrid micromachined ultrasound transducer in accordance with various embodiments.

FIG. 3 shows a flow diagram for a method of operating a hybrid micromachined ultrasound transducer in accordance with various embodiments. Though depicted sequentially as a matter of convenience, at least some of the actions shown can be performed in a different order and/or performed in parallel. Additionally, some implementations may perform only some of the actions shown. In some implementations, at least some of the operations of the method 300 can be implemented using the hybrid micromachined ultrasound transducer 102.

In block 302, an electrical signal drives the hybrid micromachined ultrasound transducer 102 to generate an ultrasound signal. The piezoelectric micromachined transducer 202 is actuated by driving two of the three electrodes of the hybrid micromachined ultrasound transducer 102. For example, electrical signal generated by the transmitters 108 drive the upper electrode 206 and the middle electrode 210 to initiate generation of an ultrasound signal by the piezoelectric micromachined transducer 202.

In block 304, the bias voltage applied to the capacitive micromachined transducer 204 is adjusted to optimize the capacitive micromachined transducer 204 for transmission. For example, the bias voltage may be reduced by lowering the DC voltage across the electrodes (e.g., the middle electrode 210 and the bottom electrode 218) of the capacitive micromachined transducer 204. By lowering the bias voltage applied to the capacitive micromachined transducer 204 the sensitivity of the capacitive micromachined transducer 204 is reduced and the deflection range of the capacitive micromachined transducer 204 is increased.

In block 306, the hybrid micromachined ultrasound transducer 102 is driven to generate an ultrasound signal. The capacitive micromachined transducer 204 is actuated by driving two of the three electrodes of the hybrid micromachined ultrasound transducer 102. For example, an electrical signal is applied to the middle electrode 210 and the lower electrode 218 to initiate generation of an ultrasound signal by the capacitive micromachined transducer 202. In some embodiments, the piezoelectric micromachined transducer 202 and the capacitive micromachined transducer 204 are simultaneously actuated by simultaneously driving the upper electrode 206, the middle electrode 210, and the lower electrode 218 to initiate simultaneous generation of ultrasound signals by both the piezoelectric micromachined transducer 202 and the capacitive micromachined transducer 204.

In block 308, reflected ultrasound signals are detected. Reflected ultrasound signals incident on the piezoelectric layer 208 cause the piezoelectric layer 208 to flex and produce a voltage across the piezoelectric layer 208. The voltage across the piezoelectric layer 208 is provided to receiver circuitry, such as the receivers and analog processing circuitry 110 via the upper electrode 206 and the middle electrode 210 in block 310.

In block 312 the bias voltage applied to the capacitive micromachined transducer 204 is adjusted to optimize the capacitive micromachined transducer 204 for ultrasound detection. For example, the bias voltage may be increased by increasing the DC voltage across the electrodes (e.g., the middle electrode 210 and the bottom electrode 218) of the capacitive micromachined transducer 204. By increasing the bias voltage applied to the capacitive micromachined transducer 204 the sensitivity of the capacitive micromachined transducer 204 is increased, and the ultrasound signal detection capability of the capacitive micromachined transducer 204 is enhanced.

In block 314, reflected ultrasound signals are detected. Reflected ultrasound signals incident on the structural plate 212 cause the middle electrode 210 to flex and change the distance to the lower electrode 218 and the voltage across the capacitive micromachined transducer 204. The voltage across the capacitive micromachined transducer 204 is provided to receiver circuitry, such as the receivers and analog processing circuitry 110 via the middle electrode 210 and the lower electrode 218 in block 316. In some embodiments, the piezoelectric micromachined transducer 202 and the capacitive micromachined transducer 204 are simultaneously applied as ultrasound receivers by receiving electrical signals from the upper electrode 206, the middle electrode 210, and the lower electrode 218.

Figure 4:
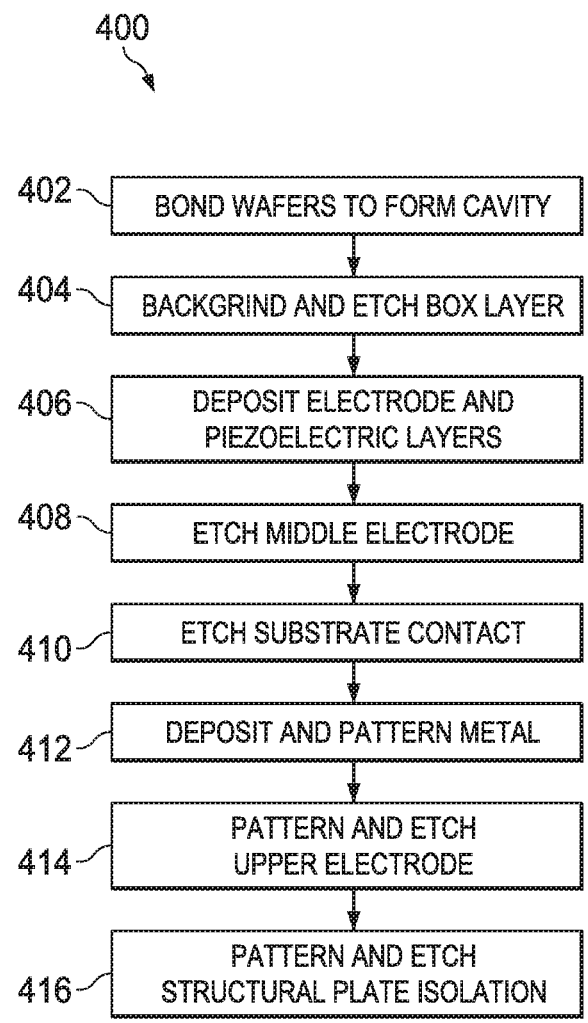
FIG. 4 shows a flow diagram for a method for fabricating a hybrid micromachined ultrasound transducer in accordance with various embodiments.

FIG. 4 shows a flow diagram for a method 400 for fabricating a hybrid micromachined ultrasound transducer in accordance with various embodiments. In some implementations, at least some of the operations of the method 400 can be performed to fabricate the hybrid micromachined ultrasound transducer 102. The method 500 is provided as an example of a fabrication process suitable for producing the hybrid micromachined ultrasound transducer 102. Some embodiments of the hybrid micromachined ultrasound transducer 102 are produced using different fabrication operations than those provided in the method 400. Though depicted sequentially as a matter of convenience, at least some of the actions shown can be performed in a different order and/or performed in parallel. Additionally, some implementations may perform only some of the actions shown. While the method 400 describes fabrication of a single hybrid micromachined transducer, in practice any number of hybrid micromachined transducers are simultaneously fabricated to produce a plurality of hybrid micromachined transducers on a die for use in the ultrasound probe 104.

Figure 5A:
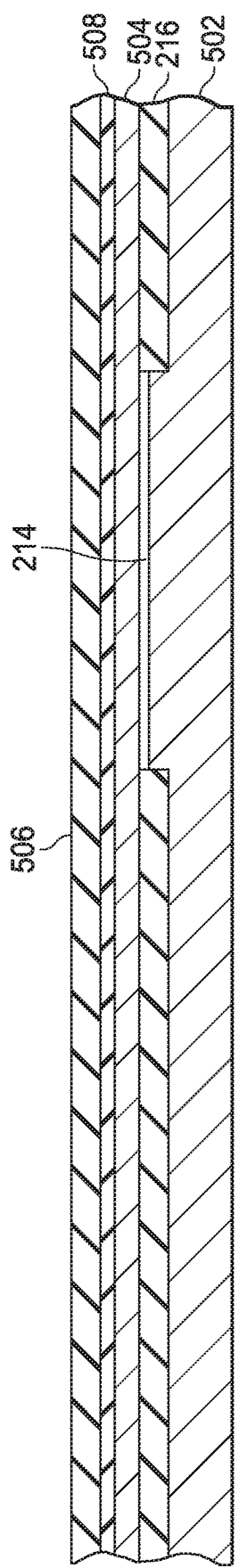
FIGS. 5A-5H show fabrication steps employed in a method for fabricating a hybrid micromachined ultrasound transducer in accordance with various embodiments.

In block 402, the cavity 214 of the capacitive micromachined transducer 204 is formed by bonding two wafers. FIG. 5A shows the wafer 502 bonded to the wafer 504 to construct the cavity 214 of the capacitive micromachined transducer 204. In some embodiments, the insulation layer 216 is provided via local oxidation of silicon in the wafer 502 to produce silicon dioxide. The insulation layer 220 (FIG. 2) is provided by a similar process in various embodiments. The wafer 502 serves as the substrate/bottom electrode 218 and the wafer 504 serves as the structural plate 212 of the capacitive micromachined transducer 204.

Figure 5B:
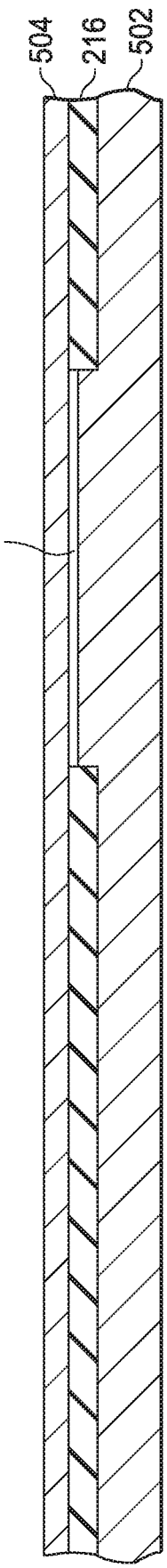

In some embodiments, the wafer 504 is a silicon-on-insulator wafer. In block 404, the handle layer and the buried oxide of the wafer 504 are removed. For example, the handle layer 506 of the wafer 504 may be removed by backgrinding and wet etching. The buried oxide layer 508 may be removed by etching. FIG. 5B shows a wafer stack resulting from removal of the handle layer 506 and the buried oxide 508 from the wafer 504.

Figure 5C:
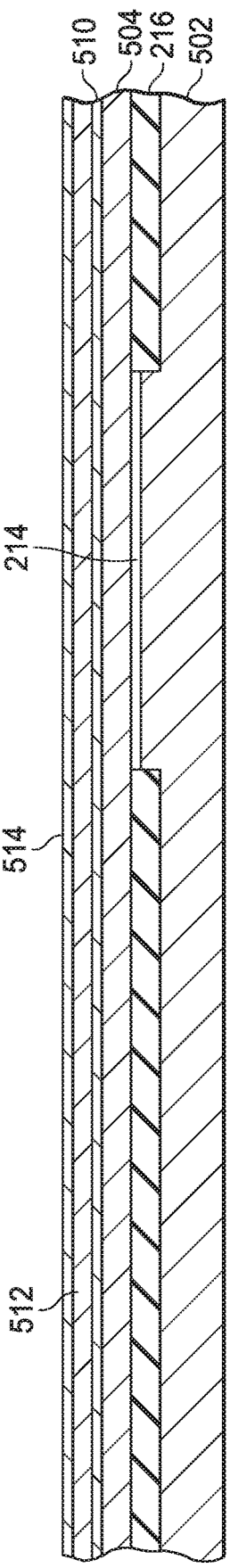

In block 406, electrode metal layers and a piezoelectric layer are deposited on top of the wafer 504. In some embodiments the metal layers are molybdenum and piezoelectric material is aluminum nitride. FIG. 5C shows a first metal layer 510 deposited atop the wafer 504. A piezoelectric layer 512 is deposited atop the first metal layer 510. A second metal layer 514 is deposited atop the piezoelectric layer 512. The middle electrode 210 will be formed from the first metal layer 510, and the upper electrode 206 will be formed from the second metal layer 514.

Figure 5D:
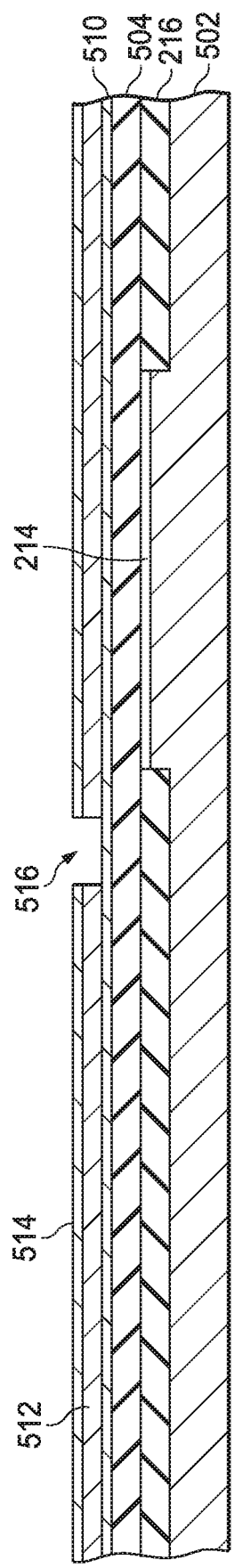

In block 408, the second metal layer 514 and the piezoelectric layer 512 are etched to expose the first metal layer 510, i.e., to provide access to the middle electrode 210. FIG. 5D shows an opening 516 etched in the second metal layer 514 and the piezoelectric layer 512 to expose the first metal layer 510.

Figure 5E:
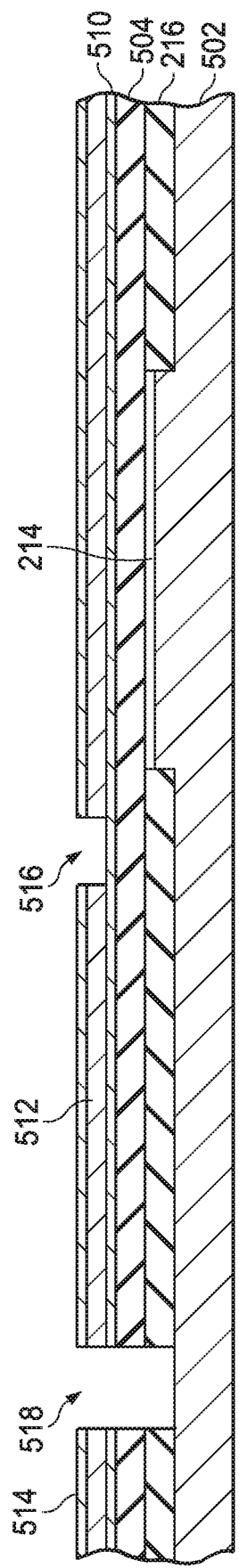

In block 410, the second metal layer 514, the piezoelectric layer 512, the first metal layer 510, the wafer 504, and the insulation layer 216 are etched to expose the substrate 502, i.e., to provide access to the lower electrode 218. FIG. 5E shows an opening 518 etched in the second metal layer 514, the piezoelectric layer 512, the first metal layer 510, the wafer 504, and the insulation layer 216 to expose the substrate 502.

Figure 5F:
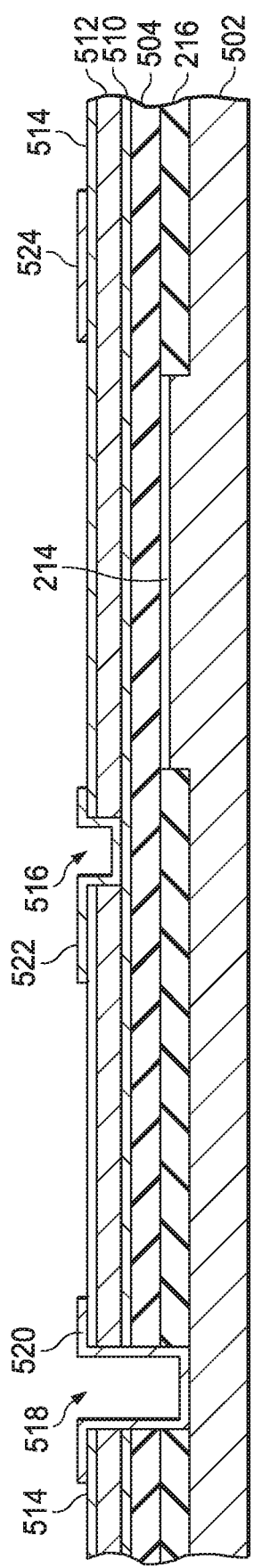

In block 412, a metal, such as aluminum, copper, or gold, is deposited to provide electrical connections for the upper electrode 206, the middle electrode 210, and the lower electrode 218. FIG. 5F shows metal 520 deposited in opening 518 to provide a plated via for electrical contact with the lower electrode 218, metal 522 deposited in opening 516 to provide a plated via for electrical contact with the middle electrode 210, and metal 5a24 deposited atop the second metal layer 514 to provide electrical contact with the upper electrode 206.

Figure 5G:
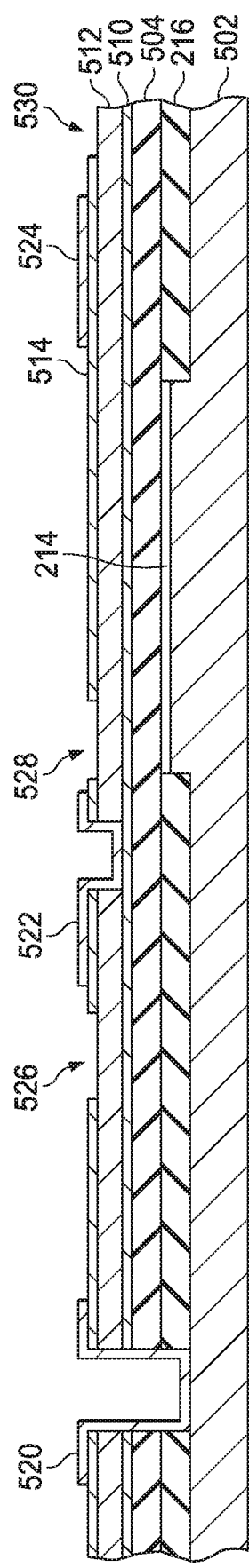

In block 514, the second metal layer 514 is etched and patterned to isolate the upper electrode 206, the middle electrode 210, and the lower electrode 218. FIG. 5G shows voids 526, 528, and 530 etched in the second metal layer 514. Void 526 isolates the lower electrode 218 from the middle electrode 210. Void 528 isolates the middle electrode 210 from the upper electrode 206. Void 530 isolates the upper electrode 206 from the lower electrode 218 (e.g., of an adjacent hybrid micromachined ultrasound transducer 102).

Figure 5H:
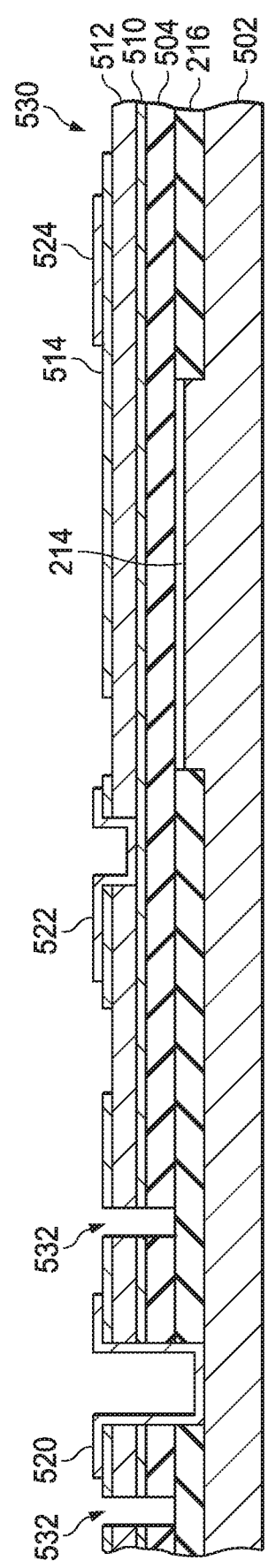

In block 516, the second metal layer 514, the piezoelectric layer 512, the first metal layer 510, and the wafer 504 are etched to isolate the structural plate 212 from the substrate 218. FIG. 5H shows openings 532 etched in the second metal layer 514, the piezoelectric layer 512, the first metal layer 510, and the wafer 504 to isolate the structural plate 212 from the substrate 218.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A micromachined ultrasound transducer, comprising:
a silicon substrate, and formed on the substrate:
a piezoelectric micromachined transducer; and
a capacitive micromachined transducer vertically stacked with the piezoelectric micromachined transducer;
wherein:
the substrate is a bottom electrode of the capacitive micromachined transducer; and
the piezoelectric micromachined transducer and the capacitive micromachined transducer comprise a common shared electrode.

2. The micromachined ultrasound transducer of claim 1, further comprising no more than three electrodes.

3. The micromachined ultrasound transducer of claim 1, wherein the bottom electrode configured to operate as a lower plate of the capacitive micromachined transducer.

4. The micromachined ultrasound transducer of claim 3, further comprising a vacuum gap formed above the bottom electrode, the vacuum gap configured to form a dielectric of the capacitive micromachined transducer.

5. The micromachined ultrasound transducer of claim 4, further comprising a structural layer disposed above the vacuum gap.

6. The micromachined ultrasound transducer of claim 4, wherein the shared electrode is disposed above the vacuum gap, and the shared electrode is configured to operate as an upper plate of the capacitive micromachined transducer.

7. The micromachined ultrasound transducer of claim 1, further comprising:
a layer of piezoelectric material; and
a top electrode disposed above the layer of piezoelectric material, the top electrode configured to operate as a first electrode of the piezoelectric micromachined transducer.

8. The micromachined ultrasound transducer of claim 7, wherein the shared electrode is disposed beneath the layer of piezoelectric material and is configured to operate as a second electrode of the piezoelectric micromachined transducer.

9. An ultrasound transducer, comprising:
a silicon substrate, and formed on the substrate:
a capacitive micromachined transducer; and
a piezoelectric micromachined transducer;
wherein:
the substrate is a bottom electrode of the capacitive micromachined transducer; and
the piezoelectric micromachined transducer is disposed above and is laterally aligned with the capacitive micromachined transducer in a stack of micromachined layers.

10. The ultrasound transducer of claim 9, comprising an intermediate electrode that is shared by the capacitive micromachined transducer and the piezoelectric micromachined transducer.

11. The ultrasound transducer of claim 10, wherein the piezoelectric micromachined transducer comprises:
a top electrode configured to operate as a first electrode of the piezoelectric micromachined transducer; and
a layer of piezoelectric material disposed beneath the top electrode.

12. The ultrasound transducer of claim 11, wherein the intermediate electrode is disposed beneath the layer of piezoelectric material and configured to operate as a second electrode of the piezoelectric micromachined transducer.

13. The ultrasound transducer of claim 10, wherein the capacitive micromachined transducer comprises a structural plate disposed beneath the intermediate electrode, and wherein the intermediate electrode is configured to operate as a first electrode of the capacitive micromachined transducer.

14. The ultrasound transducer of claim 13, wherein the capacitive micromachined transducer comprises a vacuum gap formed beneath the structural plate, wherein the vacuum gap is configured to form a dielectric of the capacitive micromachined transducer.

15. The ultrasound transducer of claim 13, wherein the bottom electrode is configured to operate as a second electrode of the capacitive micromachined transducer.

16. A method for operating a hybrid micromachined ultrasound transducer, comprising:
    driving a first electrode and a second electrode of a first micromachined transducer of the hybrid micromachined ultrasound transducer to generate an ultrasonic signal;
    detecting a reflection of the ultrasonic signal via a second micromachined transducer that is vertically stacked with the first micromachined transducer in the hybrid micromachined ultrasound transducer; and
    providing an electrical signal representative of the detected reflection of the ultrasonic signal via the second electrode and a third electrode, wherein the second electrode serves as an electrode of the first micromachined transducer and an electrode of the second micromachined transducer.

17. The method of claim 16, further comprising driving the third electrode to simultaneously generate an ultrasonic signal via the second micromachined transducer and the first micromachined transducer.

18. The method of claim 16, further comprising simultaneously detecting the reflection of the ultrasonic signal via the first micromachined transducer and the second micromachined transducer.

19. The method of claim 18, further comprising providing an electrical signal representative of the detected reflection of the ultrasonic signal via the first electrode, the second electrode, and the third electrode.

20. The method of claim 16, wherein the first micromachined transducer is a piezoelectric micromachined transducer and the second micromachined transducer is a capacitive micromachined transducer.

\* \* \* \* \*